United States Patent [19]

Bichel

[11] Patent Number: 4,716,890

[45] Date of Patent: Jan. 5, 1988

[54] CHIROPRACTIC THRUSTER

[76] Inventor: Ronald A. Bichel, 3141 Hwy. K South, Hartford, Wis. 53027

[21] Appl. No.: 823,771

[22] Filed: Jan. 29, 1986

[51] Int. Cl.⁴ .......................... A61F 5/00; A61H 23/04

[52] U.S. Cl. .......................................... 128/55; 128/69

[58] Field of Search ........................ 128/53, 54, 55, 51, 128/68, 69

[56] References Cited

U.S. PATENT DOCUMENTS

| | | | |
|---|---|---|---|
| 2,048,220 | 7/1936 | Redding | 128/69 |
| 2,076,410 | 4/1937 | McGerry | 128/55 |
| 2,078,159 | 4/1937 | Redding | 128/54 |
| 2,204,259 | 6/1940 | Schuster et al. | 128/55 |
| 3,955,563 | 5/1976 | Maime | 128/55 |
| 4,016,873 | 4/1977 | Anderson | 128/53 |
| 4,116,235 | 9/1978 | Fuhr et al. | 128/69 |
| 4,445,503 | 5/1984 | Havstad | 128/55 |
| 4,461,286 | 7/1984 | Sweat | 128/69 |
| 4,549,535 | 10/1985 | Wing | 128/55 |
| 4,566,441 | 1/1986 | Havstad | 128/55 |

*Primary Examiner*—Edgar S. Burr
*Assistant Examiner*—Tonya Lamb
*Attorney, Agent, or Firm*—Thomas F. Kirby

[57] ABSTRACT

A chiropractic thruster for use in chiropractic treatment to apply controlled impact forces or thrusts to a human body comprises a rubber tipped free-floating punch, the length of stroke of which can be adjusted to control the force applied to the body. The punch delivers one stroke whenever the trigger of a three-way poppet valve is depressed and causes a burst of compressed air to flow from a relatively large compressed air reservoir in the thruster handle to one side of a spring-biased piston in a relatively smaller air cylinder located in the thruster. The piston comprises a piston rod which drives the punch and which, when the piston is biased to retracted position, is spaced from the inner end of the punch by a predetermined distance.

6 Claims, 5 Drawing Figures

CHIROPRACTIC THRUSTER

BACKGROUND OF THE INVENTION

1. Field of Use

This invention relates generally to a chiropractic thruster for use in chiropractic treatment to apply impact forces or thrusts to a human body.

2. Description of the Prior Art

Percussor or impact devices of the aforesaid character are known and the following patents and article show the state of the art.

U.S. Pat. No. 1,657,765 issued in 1928 to Pasque discloses an electromechanical massage, vibratory or percussor apparatus which effects repeated reciprocatory motion of an adjustally positionable impact head in response to rotation of a motor-driven cam and the stroke length of the impact head can be adjusted.

U.S. Pat. No. 2,078,159 issued in 1937 to Redding discloses a vertebral adjuster in which a reciprocally movable spring-biased head delivers a single impact whenever a trigger-operated pin releases a piston which is driven in the impact direction by compressed air in a reservoir. The piston is returned to its start position by gravity when the device is tilted upwardly manually while the trigger is still depressed.

U.S. Pat. No. 2,204,259 issued in 1940 to Schuster et al discloses a spinal adjustment device wherein a cam driven by an electric motor imparts one blow to an adjustably positionable rubber-tipped reciprocable rod, spring-loaded at each end, each time a trigger-operated lever mechanically raises the cam into rod-striking position.

U.S. Pat. No. 3,955,563 issued in 1976 to Maione discloses a pneumatic percussor wherein a spring-return plunger reciprocally vibrates in response to compressed air pulses provided through an electronically pulsed air supply control valve.

U.S. Pat. No. 4,016,873 issued in 1977 to Anderson discloses a pneumatic impacter wherein a rubber-tipped reciprocally movable spring-biased plunger delivers a single stroke in response to each operation of a trigger-operated valve which admits compressed air from a reservoir to a piston on the rear end of the plunger.

U.S. Pat. No. 4,461,286 issued in 1964 to Sweat discloses a mechanical chiropractic instrument wherein a reciprocally movable thrust pin is propelled outwardly by a spring to impart a single blow each time a trigger is actuated to release a spring-loaded adjustably positionable percussion device which strikes the trust pin and such instrument needs to be manually reset to recharge the spring after each blow.

An article in the November/December 1984 edition of *The Digest of Chiropractic Economics* entitled "The Force Of The Activator Adjusting Instrument" by Mark L. Duell, B.S., D.C., discloses an activator adjusting instrument and test data relative thereto.

SUMMARY OF THE INVENTION

A chiropractic thruster for use in chiropractic treatment to apply controlled impact forces or thrusts to a human body comprises a rubber tipped free-floating punch, the length of stroke of which can be adjusted between ¼" and zero. The punch travel can be set to some selected predetermined adjustable distance (determined by stroke adjustment means on an adjustment screw in which the punch is slidably mounted) to control the force applied to the body. The punch delivers one stroke whenever the trigger of a high speed three-way poppet valve is depressed and causes a powerful burst of compressed air to flow from a compressed air reservoir in the thruster handle to one side of a spring-biased piston in an air cylinder located in the thruster. The cylinder volume on said one side of the piston is less than the volume of the reservoir. The piston comprises a piston rod which drives the punch and which, when the piston is biased to retracted position, is spaced from the inner end of the punch.

The thruster offers several advantages over prior art. For example, the stroke length of the punch is adjustable and the force applied thereto is adjustable. No manual resetting is required after each stroke is delivered and automatic resetting occurs very rapidly. The poppet valve rapidly delivers a high volume of compressed air. Wear on operating parts is minimal. Adjustments remain constant, once established. The entire thruster is designed to facilitate relatively easy and economical manufacture, assembly and use and is easily disassembled for servicing. Other objects and advantages will hereinafter appear.

DRAWINGS

DESCRIPTION OF A PREFERRED EMBODIMENT

Figure 1:
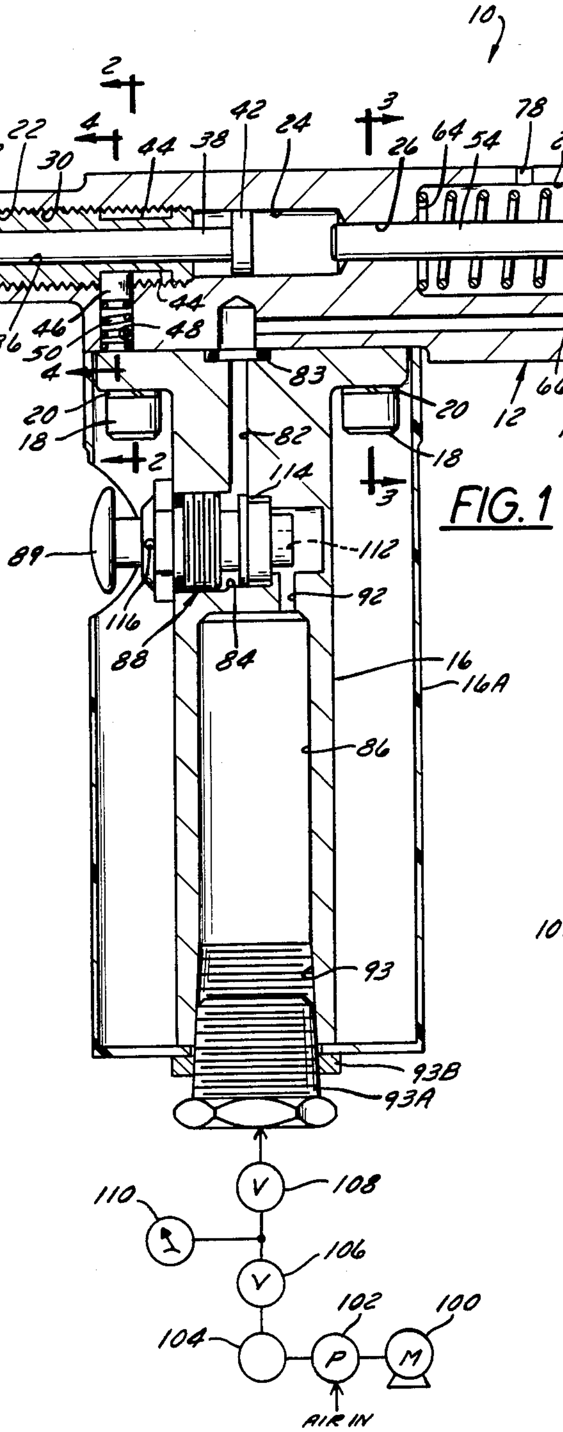
FIG. 1 is a cross-section view of a thruster in accordance with the invention and showing the poppet valve closed and the piston spring-biased to retracted position.
Figure 5:
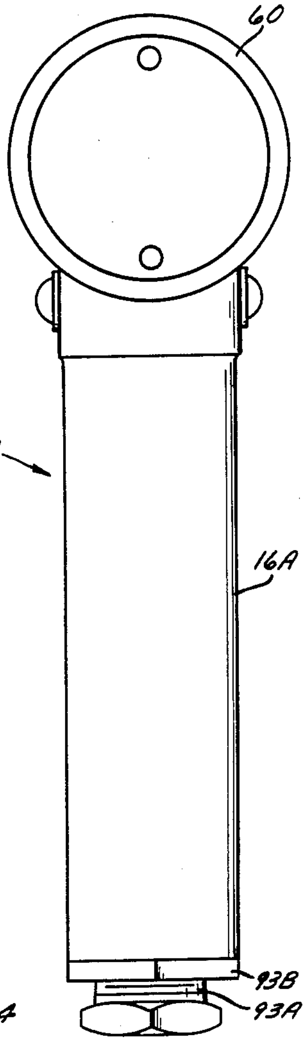
FIG. 5 is an elevation view of the rear end of the thruster.
Figure 2:
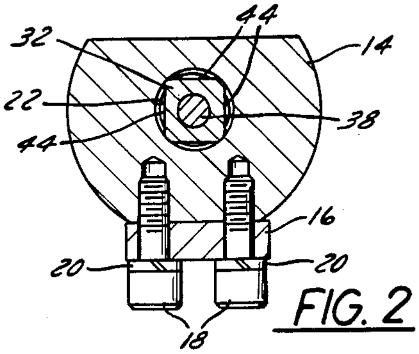
FIG. 2 is a cross-section view taken on line 2—2 of FIG. 1.
Figure 3:
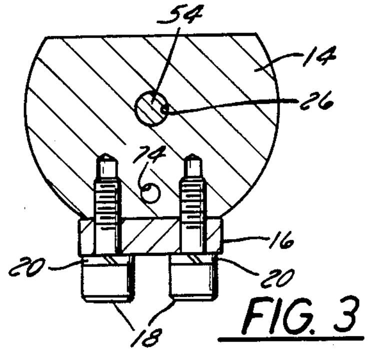
FIG. 3 is a cross-section view taken on line 3—3 of FIG. 1.

Referring to FIGS. 1 and 5, numeral 10 designates a chiropractic thruster in accordance with the invention. Thruster 10 comprises a supporting structure 12 having a cylinder member 14 which is releasably connected to a handle member 16 by four screws 18 which have lock washers 20 thereon. A plastic handle grip 16A surrounds member 16.

Cylinder member 14 has a bore extending horizontally therethrough from one end to another which is divided into four axially aligned cylindrical bore sections 22, 24, 26 and 28 of different diameters.

Figure 4:
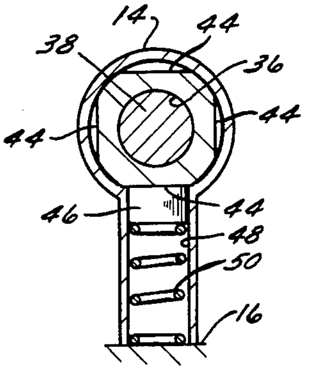
FIG. 4 is an enlarged cross-section view taken on line 4—4 of FIG. 1.

Bore section 22 in cylinder member 14 is internally threaded at 30 and receives therein a hollow rotatable adjustment screw 32 which has external threads 34 which enable it to be rotated and thus axially shifted to selected positions. Screw 32 has a bore 36 in which an elongated punch 38 is slideably mounted. Punch 38 has a resilient member 40, preferably rubber, and a retainer nut 41 mounted at its outer end and has a flange 42 at its inner end which limits axial travel of the punch relatively to screw 32. Punch 38 is "free floating" in bore 36 but, in use, is maintained in retracted position, except when activated, because the member 40 is pressed against the patient's body 11, as in FIG. 1. As FIGS. 1 and 4 show, screw 32 is provided near its inner end with four flat surfaces 44 which are adapted to engage with a spring-biased detent or lug 46 which is slideably mounted in a drilled hole 48 formed in cylinder member 14. A compression spring 50, which is inserted in hole 48 before members 14 and 16 are joined by the screw 18, biases detent 46 against whichever flat surface is presented to it as adjustment screw is rotated and serves to releasably lock screw 32 (and punch 38 thereon) in selected positions.

Bore section 24 in cylinder member 14 slideably receives flange 42 of punch 38 and is of such a length as to define a predetermined constant distance between the inner end of punch 38 (when the latter is biased to its retracted position) and the free end of a piston rod 54, hereinafter described, which, when actuated, effects movement of punch 38 to its extended position. The predetermined distance is the same as the stroke of piston rod 54 and this distance and the rate of speed of travel of piston rod 54 determine the force applied to punch 38. Since screw 32 is adjustable for about ¼ inch, the distance which punch 38 can travel, when imparted by piston rod 54 can be varied, for example, between a maximum of one-fourth (¼) of an inch and a minimum of zero (0). However, punch 38 travels a distance which is equal to the difference between the length of adjustment screw 32 and the distance between the inner surface of nut 41 and flange 42 on punch 38, which difference is on the order of up to one-fourth (¼) inch, depending on the position of nut 41.

Bore section 26 in cylinder member 14 slideably receives the piston rod 54 which has one end connected to a piston 56 which is slideably mounted for reciprocation in cylindrical bore section 28 in cylinder member 14 between two positions, namely, an initial position shown in FIG. 1 at the right end of bore section 28 and an extended position (not depicted) to the left thereof. Bore section 28 is closed at one end by an internally threaded end cap 60 which screws onto external threads 62 on the right end of cylinder member 14. Bore section 28 is closed at its other end by an end wall 64 and piston rod 54. Thus, a gas (compressed air) cylinder 66 is provided. Piston 56 is biased toward (and into) its initial position by means of a helical compression spring 68 disposed therearound and engaged with end wall 64. Piston 56 is movable from its initial position against the spring bias (to effect movement of piston rod 54 and punch 38) in response to entry of compressed gas into an annular space 70 formed on the inner surface of end cap 60 and confronting the surface 57 of piston 56. Piston 56 has a gas-tight O-ring seal 59 thereon.

Gas cylinder 66 has a gas inlet port 72 at the point where a drilled passage 74 in cylinder member 14 communicates with annular space 70 in end cap 60. Gas cylinder 66 has a gas exhaust port 78 on its upper side, intermediate its ends and nearer to the other (left) end of the gas cylinder 66 than gas inlet port 72. Expanding compressed gas entering gas inlet port 72 forces piston 54 leftward (with respect to FIG. 1) but piston surface 57 never moves past gas exhaust port 78 and the gas in gas cylinder 66 only on the left side of piston 54 escapes through port 78. Leftward movement of piston 56 is stopped by punch 38. The maximum volume of that portion of gas cylinder 66 between end cap 60 and the plane at which the surface 57 stops, as above-described, bears a relationship to the volume of a compressed gas reservoir 86, as hereinafter described.

Turning now to the handle member 16 of supporting structure 12 of thruster 10 shown in FIG. 1, it is seen to have a bore extending vertically therethrough from one end to another which is divided into three major axially aligned bore sections 82, 84 and 86.

Bore section 82 takes the form of a drilled passage which communicates by intersection with passage 74 in cylinder member 14 to provide a gas flow path. A gas-tight O-ring seal 83 is provided where they join.

Bore section 84, which extends inwardly from a side of handle member 16 and is in communication with passage 82, is adapted to receive and support a manually operable three-way poppet valve 88 which has an externally extending actuator or trigger 89.

Bore section 86, formed by drilling inwardly from the bottom of handle member 16, serves as a compressed gas reservoir. Reservoir 86 is connected at its upper end by a small drilled passage 92 to bore section 84 and is provided at its lower end with internal threads 93 which receive a bushing 93A (having a lock nut 93B) to adapt it for connection to a source of compressed gas. The volume of gas reservoir 86 is substantially greater (i.e., on the order of at least about 1½ times greater) than the maximum volume of the afore-described portion of gas cylinder 66 between piston surface 57 and cap 60. As FIG. 1 shows, the source of compressed gas for reservoir 86 may take the form of an electric motor 100 which drives an air compressor pump 102 to supply compressed air to a storage tank 104 from which it is then continously supplied through a regulator valve 106 and a manually controlled shut-off valve 108 to reservoir 86. An air pressure gauge 110 is provided.

The arorementioned manually operable three-way poppet valve 86 having trigger 89, which may take the form of a commercially available valve, comprises a valve gas inlet port 112, a normally-closed valve gas outlet port 114, and a normally-open valve gas exhaust port 116. Inlet port 112 and outlet port 114 are connected in series between gas outlet port 92 of reservoir 86 and gas inlet port 72 of gas cylinder 66 through passages 82 and 74. Exhaust port 116 is also connected to gas inlet port 72 of cylinder 66 internally of the valve.

The trigger 89 for operating poppet valve 88 is movable between a trigger-released position wherein valve gas outlet port 114 is closed and valve gas exhaust port 116 is open, and a trigger-actuated (depressed) position wherein valve gas outlet port 114 is open and valve gas exhaust port 116 is closed.

Assuming that reservoir 86 is charged with compressed air, the valve gas outlet port 114, when opened by depression of trigger 89, operates to admit air from reservoir 86 to cylinder 66 whereby piston 56 advances from its initial position and imparts a single blow to the inner end of punch 38. Valve gas outlet port 114, when closed by release of trigger 89, operates to bleed air from cylinder 66 through valve exhaust port 116 to atmosphere to permit piston 56 to be biased back to its initial position by spring 68. The actuator 10 is then in readiness for a repeat of the above-described cycle when trigger 89 is again depressed.

Adjustment of the length of the stroke of punch 38 is effected by rotating adjustment screw 32 in the appropriate direction so as to change the distance between flange 42 on punch 38 and the inner end of screw 32. In use, the resilient member 40 of punch 38 is pressed against the surface of the patient's body 11 so that punch 38 assumes the position in FIG. 1 before the trigger 89 is operated. When the trigger 89 is depressed, the piston rod 54 travels its full stroke and forcefully strikes punch 38, but the punch can only move some distance between zero and one-fourth (¼) of an inch, depending on how screw 32 has been adjusted.

I claim:

1. A chiropractic thruster comprising:

a supporting structure;

a punch mounted for sliding reciprocable movement in said structure and having an outer end extending from said structure and an inner end within said structure:

a gas cylinder on said structure and having a gas inlet port near one end and a gas exhaust port near its other end;

a piston slideably mounted for reciprocable movement in said cylinder between an initial position at one end of said gas cylinder and another position near the other end of said gas cylinder;

biasing means for resiliently biasing said piston toward said one end of said cylinder to said initial position;

a piston rod connected at one end to said piston and having a free end extending from said cylinder, said free end of said piston rod being spaced apart a predetermined distance from said inner end of said punch when said piston is biased to said one end of said cylinder;

a compressed gas reservoir on said structure and having a gas inlet port and a gas outlet port, said reservoir having a larger volume than the maximum volume of that portion of said gas cylinder located between said gas inlet port and said piston;

a poppet valve mounted on said structure and having a valve gas inlet port, a normally-closed valve gas outlet port and a normally open valve exhaust port, said valve inlet port and said valve outlet port being connected in series betwen said gas outlet port of said reservoir and said gas inlet port of said cylinder, said valve gas exhaust port being connected to said gas inlet port of said cylinder; and a trigger mounted on said structure for operating said valve and movable between a trigger-released position wherein said valve gas outlet port is closed and said valve gas exhaust port is open, and a trigger-actuated position wherein said valve gas outlet port is open and said valve gas exhaust port is closed;

said valve gas outlet port when open operating to admit air from said reservoir to said cylinder whereby said piston advances toward said other position and imparts a single blow to said inner end of said punch, said valve gas outlet port when closed operating to bleed air from said cylinder to atmosphere to permit said piston to be biased to said initial position.

2. A chiropractic thruster according to claim 1 further including adjustment means for adjustably positioning said punch relative to said supporting structure to thereby change the length of stroke of said punch.

3. A chiropractic thruster according to claim 2 wherein said adjustment means comprises means to move said punch to selected axial positions and means to releasably lock said punch in any of said selected positions.

4. A chiropractic thruster according to claim 3 wherein said means to move said punch comprises a threaded bore in said structure, an externally threaded hollow adjustment screw threadably mounted in said bore and rotatable to selected axial positions relative to said bore, said adjustment screw having a bore therein in which said punch is slideably mounted for movement between two extreme positions;

and wherein said means to releasably lock said punch in any of said selected positions comprises interengaging spring-biased detent means between said structure and said adjustment screw.

5. A chiropractic thruster according to claim 1 wherein said supporting structure comprises a cylinder member and a handle member connected to said cylinder member; wherein said punch, said gas cylinder, said piston, said piston rod and said biasing means are mounted on said cylinder member; and wherein said compressed air reservoir, said poppet valve and said trigger are mounted on said handle member.

6. A chiropractic thruster according to claim 5 including means for releasably connecting said cylinder member to said handle member, and wherein each of said members includes a passage, which passages interconnect-to provide a flow path from said gas inlet port of said cylinder to said valve gas outlet port and to said valve gas exhaust port of said poppet valve.

* * * * *